United States Patent

Schilder et al.

Patent Number: 5,686,090
Date of Patent: Nov. 11, 1997

[54] MULTI-LAYERED IMPLANT

[75] Inventors: Lothar Schilder; Hermann Dahlke, both of Hamburg, Germany

[73] Assignee: Ethicon, Inc., Somerville, N.J.

[21] Appl. No.: 570,272

[22] Filed: Dec. 11, 1995

Related U.S. Application Data

[63] Continuation of Ser. No. 187,565, Jan. 27, 1994, abandoned.

[30] Foreign Application Priority Data

Jan. 28, 1993 [DE] Germany .......................... 43 02 818.7

[51] Int. Cl.⁶ .................................................... A61F 2/00
[52] U.S. Cl. ............................................ 424/423; 424/422
[58] Field of Search .............................. 424/422–427, 424/435, 473; 604/378

[56] References Cited

U.S. PATENT DOCUMENTS

| | | | |
|---|---|---|---|
| 4,116,241 | 9/1978 | Theeuwes | 128/260 |
| 4,200,098 | 4/1980 | Ayer | 128/260 |
| 4,900,552 | 2/1990 | Sanvordeker | 424/422 |
| 5,310,559 | 5/1994 | Shaw | 426/448 |

FOREIGN PATENT DOCUMENTS 0030513  2/1986  Japan .

*Primary Examiner*—Gollamudi S. Kishore
*Attorney, Agent, or Firm*—Emil Richard Skula

[57] ABSTRACT

A multi-layered implant has at least two layers, of which at least two have a different porosity. A woven or knitted mesh, e.g., can be provided completely or partly with a porous fleece layer on one side or on both sides. The porosity can vary within a fleece layer. A layer of the multi-layered implant can also consist of a film. Resorbable and non-resorbable substances are considered as materials.

2 Claims, 6 Drawing Sheets

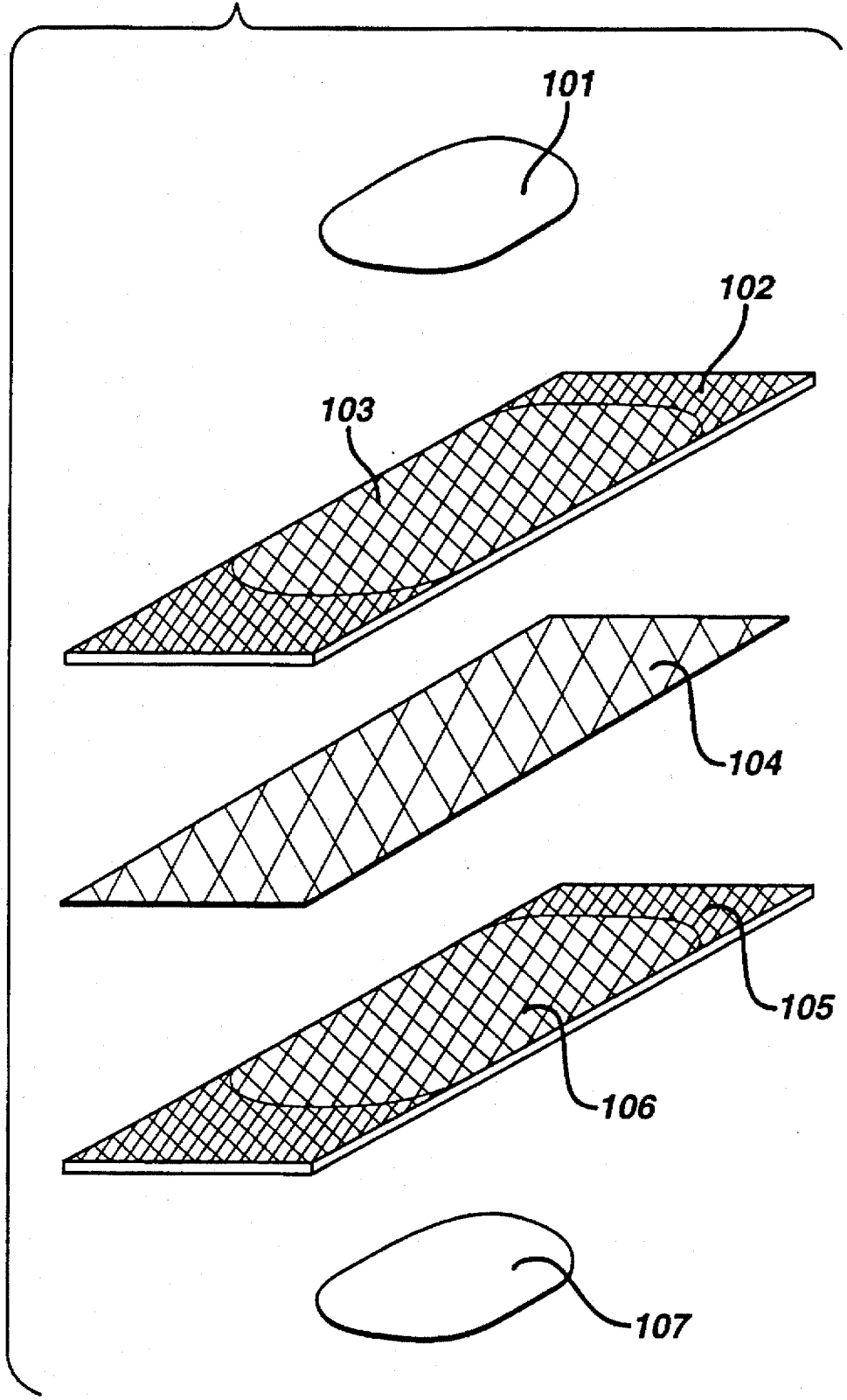

MULTI-LAYERED IMPLANT

This is a continuation of application Ser. No. 08/187,565, filed Jan. 27, 1994 now abandoned.

The invention relates to a multi-layered implant.

Conventional, homogeneous implants are implanted into the body during an operation. If they consist of a porous or resorbable material, tissue grows into the pores or in the place of the implant during the healing process and thus forms a new tissue structure. With non-resorbable implants having cavities or guiding structures, a physiological cell increase can no longer take place at a specific point in time because the non-resorbable implant does not permit complete regeneration. There is thus a tendency towards an amorphous and undirected fresh tissue formation; cicatrisation and shrinkages occur. The outcome can be inadequate tissue strength, which can even lead to complications if the implant consists of a non-resorbable material and thus itself ensures some mechanical stability. Therefore, the natural biological function of the combination of the implant and the body's own tissue does not correspond to that of the original sound tissue.

The object of the invention is to provide an implant which, at the different phases of tissue regeneration, has a selective and differentiated influence on the value and speed of tissue growth.

This object is achieved by a multi-layered implant with the features of claim 1. Advantageous versions emerge from the subsidiary claims.

The multi-layered implant according to the invention has at least two layers, of which at least two have a different porosity. The structure of the implant can thus be specifically matched to the tissue regeneration process in the body where the implant is implanted, and a desired growing-in of the tissue can be controlled. For example, rapidly-growing cell units can quickly advance from one side of the implant into a layer with large pores, while on the other side a layer of insignificant porosity, e.g. a film, can completely prevent a penetration by cells. The several layers of the implant according to the invention can consist of various materials, resorbable and non-resorbable, which in turn can be degraded at different speeds. The stimulus which the implant provides to form new tissue does not have an inhibiting influence, given a suitable choice of material, porosity, thickness and dimensions of the individual layers and of the layer sequence and overall shape of the implant, but can be selectively matched to the healing processes, which results in an accelerated and directed tissue proliferation.

The make-up and external shaping of an implant according to the invention which is implanted during a given operation are thus based on the type and shape of the original tissue structures to be replaced and thus differ from case to case. Through a suitable choice of material and structure of the individual layers, the implant according to the invention can be matched to the given biological conditions, so that the newly-forming tissue is again differentiated (high value) and, in a favourable case, has the same directed structure as the original sound tissue.

In a preferred version of the multi-layered implant according to the invention, a woven or knitted mesh (lattice) is completely or partly provided with a porous fleece layer on one side. The porosity of the fleece layer lies in the range between 100 and 1000 l/(m² s) gas flow, measured with an inlet pressure of 200 Pa, a test surface of 50 cm² and a test thickness of 1 mm. With this make-up, the mesh forms a layer of coarse porosity through which the tissue will grow virtually unhindered. The speed of tissue proliferation, on the other hand, can be controlled via the porosity of the fleece layer. The tissue thus tends to grow more quickly into a material with large porosity than into a material with small porosity. The mesh and the fleece layer can consist of a resorbable or a non-resorbable material. If, for example, the fleece layer is resorbable but the mesh is not, the mesh remains the only constituent of the implant in the body after some time and can where necessary ensure an additional permanent mechanical stability.

In another preferred version, a woven or knitted mesh is completely or partly provided with a porous fleece layer on both sides, and the two fleece layers can have a different porosity. The fleece layers can also have different shapes or outlines. The porosity within a fleece layer can also vary. Through suitable matching of these variables, a multi-layered implant according to the invention can be selectively prepared for a given use.

With another design of the multi-layered implant according to the invention, a porous fleece layer, which completely or partly fills the mesh, is located on one side of a woven or knitted mesh, while a film with a thickness between 10 and 50 μm is deposited on the other side. Such a film prevents mis-growths to the adjacent tissue and also reduces adhesion, as the tissue cells cannot penetrate the implant from the side of the implant which is provided with the film. If the film is resorbable, this effect lasts for only a certain period. However, under certain circumstances this is enough to prevent rapidly-growing cell units from advancing into the implant, while, from the other side, slowly-growing cell units grow into the porous fleece layer, which they would be prevented from doing without the film by the advancing, rapidly-growing cell units.

Other structures of a multi-layered implant according to the invention having films are also possible. Thus, a woven or knitted mesh can be provided completely or partly with a fill on one side or on both sides. With an implant which has at least one fleece layer, one of the fleece layers can be completely or partly coated with a film. Such an implant can otherwise have one of the structures listed above, i.e. can contain a mesh. Alternatively, versions are also conceivable which consist merely of two layers, namely a film, i.e. a layer with small or insignificant porosity, and a fleece layer.

The individual layers of the multi-layered implant according to the invention can each consist of a resorbable or non-resorbable material. This applies to the mesh, a fleece layer or a film. Suitable as resorbable material is e.g. preferably Polyglactin, Polydioxanone or Poliglecaprone 25 or a combination of these materials.

Polypropylene or polyester can be used as non-resorbable material.

The following examples, which are explained with the help of drawings, serve to demonstrate the variety of possible structures of the multi-layered implant according to the invention.

BRIEF DESCRIPTION OF THE DRAWINGS

FIG. 1 shows a first version of a multi-layered implant according to the invention. A woven or knitted mesh (lattice) 12 is provided on one side with a fleece 11 which has a porosity of 1000 l/m² s. On the other side of the mesh 12 there is a fleece 13 with the porosity 100 l/m² s. The gas throughflow which results if a fleece layer with a test surface of 50 cm² and a test thickness of 1 mm is exposed to the gas at an inlet pressure of 200 Pa is given as a measure for the porosity.

Figure 2:
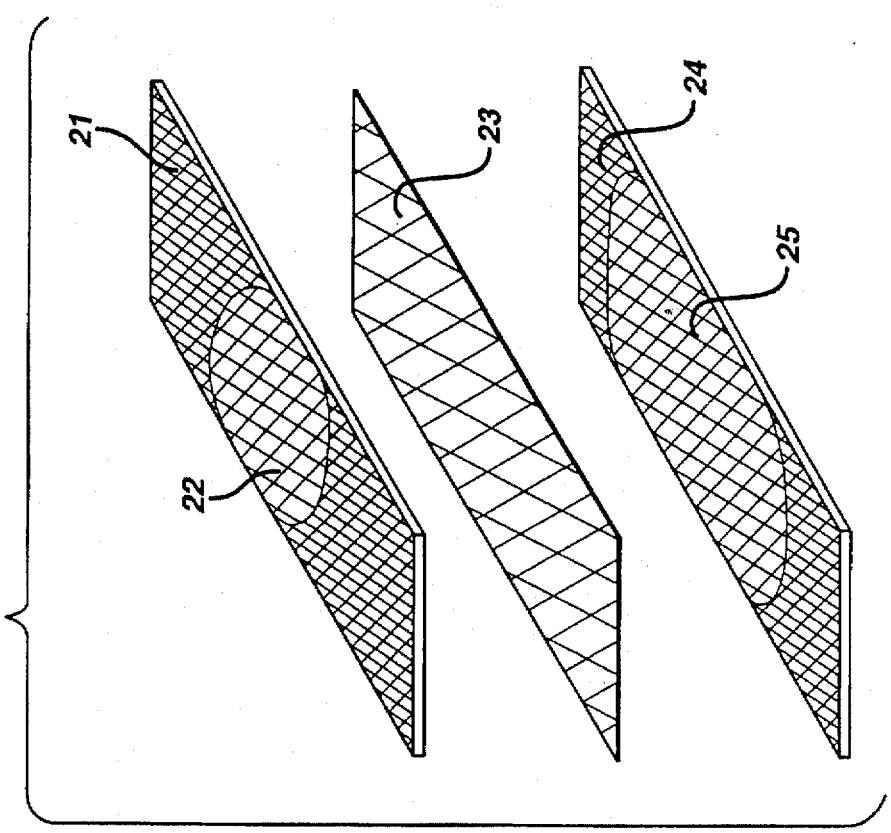
Figure 1:
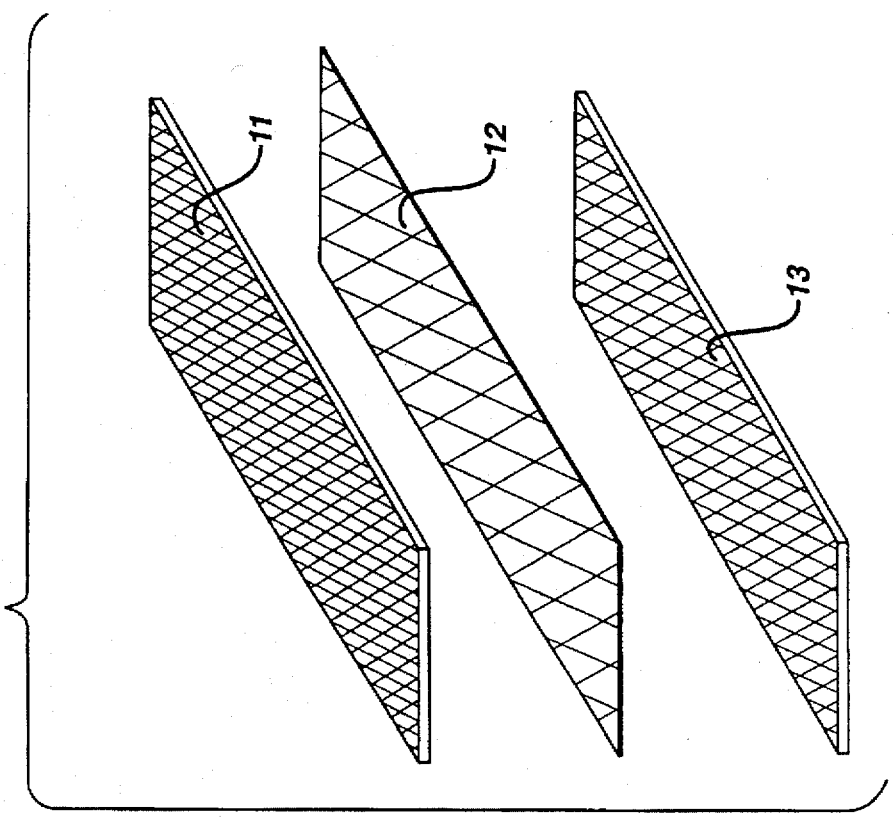
FIG. 1 an exploded view of a multi-layered implant which consists of a mesh and two fleece layers, FIG. 2 an exploded view of a multi-layered implant which consists of a mesh and two fleece layers of varying porosity, FIG. 3 an exploded view of a multi-layered implant which consists of a mesh, a fleece and a film, FIG. 4 an exploded view of a multi-layered implant which consists of a mesh, a fleece of varying porosity and a film, FIG. 5 an exploded view of a multi-layered implant which consists of a mesh and a film, FIG. 6 an exploded view of a multi-layered implant which consists of a mesh and a film whose surface is smaller than that of the mesh, FIG. 7 an exploded view of a multi-layered implant which consists of a fleece and a film, FIG. 8 an exploded view of a multi-layered implant which consists of a fleece of varying porosity and a film, FIG. 9 an exploded view of a multi-layered implant which comprises a mesh and two fleece layers, each of which is coated with a film, and FIG. 10 an exploded view of a multi-layered implant which comprises a mesh and two fleece layers of varying porosity, a partial region of each fleece layer being coated with a film.

With the embodiment represented in FIG. 2, the upper fleece layer has two zones with different porosity. Zone 21 consists of a fleece with a porosity of 1000 l/m² s, while zone 22 contains a fleece with the lower porosity 200 l/m² s. A fleece layer with two zones 24 (porosity 800 l/m² s) and 25 (porosity 300 l/m² s) is deposited on the other side of a mesh 23. It must be borne in mind that the outlines of zones 22 and 25 are different, to optimize the matching of the implant to the given conditions.

Figure 3:
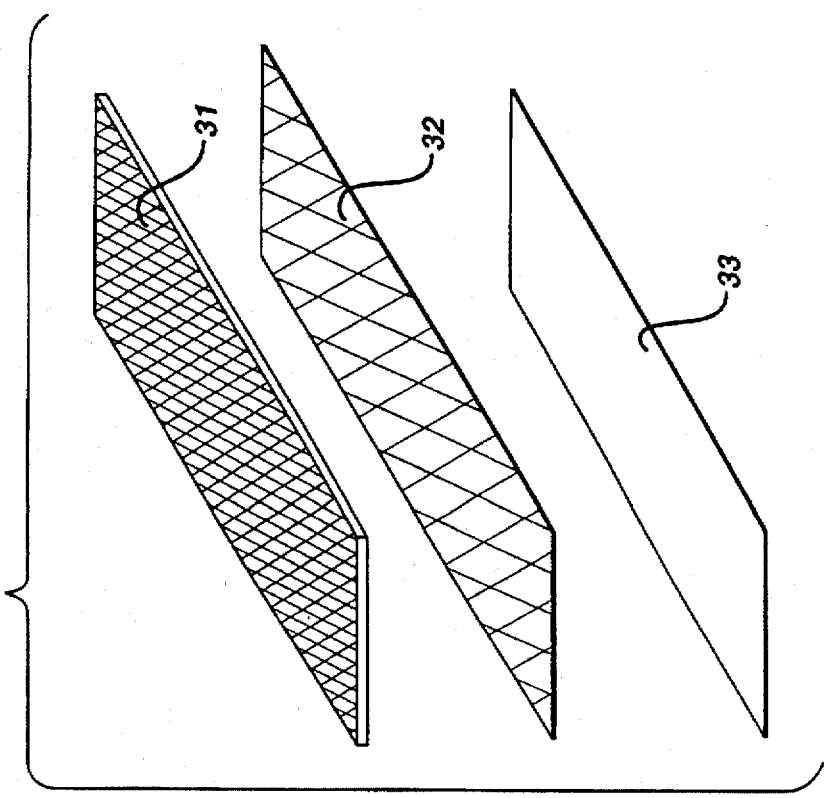

FIG. 3 shows a multi-layered implant which consists of a homogeneous fleece 31, a mesh 32 as middle layer and a film 33.

Figure 4:
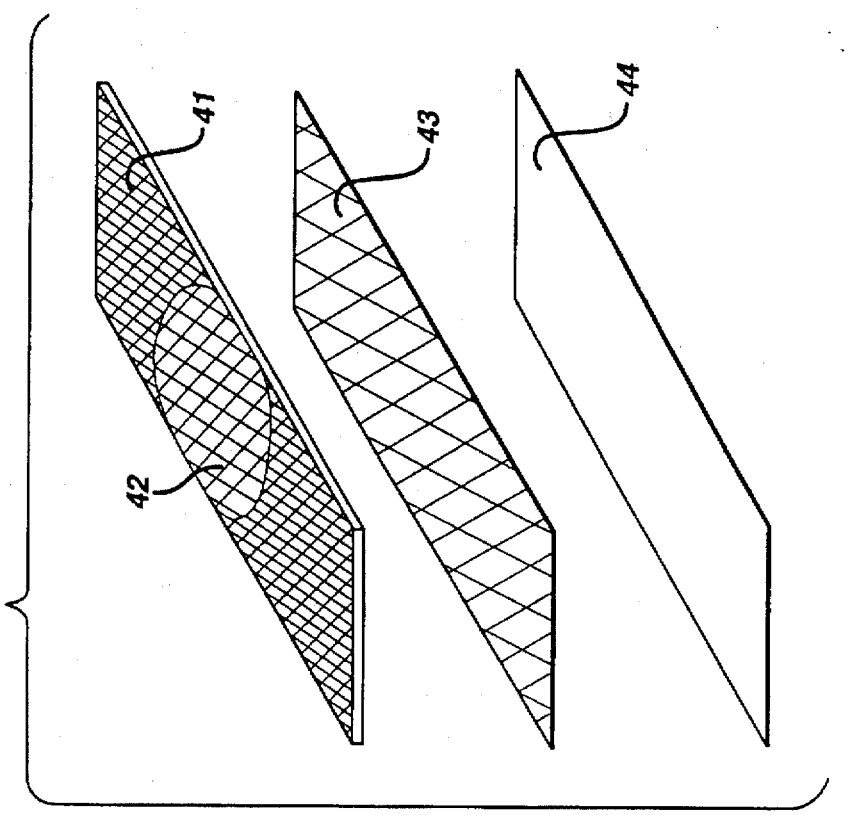

FIG. 4 shows a multi-layered implant in which the upper layer again has two zones consisting of fleece with different porosity, namely the peripheral zone 41 (porosity 100 l/m² s) and the central zone 42 (porosity 500 l/m² s). A woven or knitted mesh 43 serves as middle layer. A film 44 is located on the other side of the mesh 43.

Figure 5:
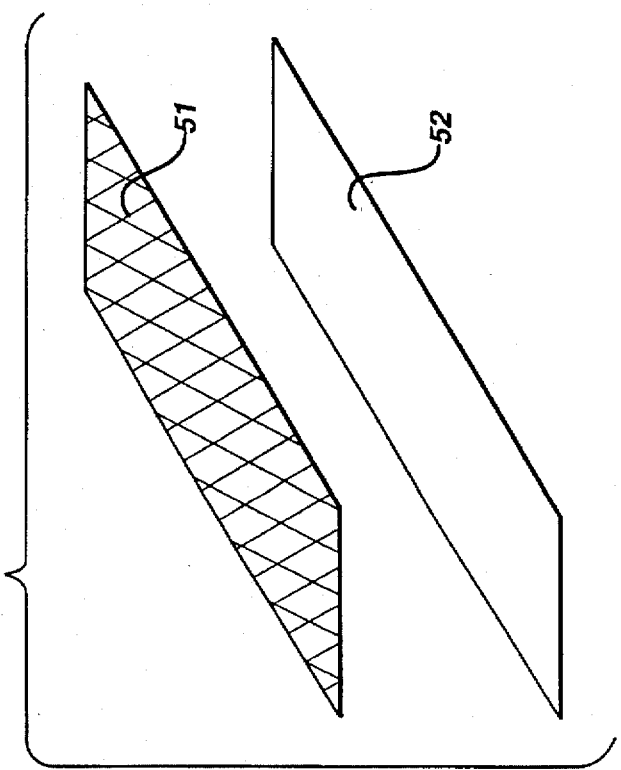

The implant from FIG. 5 consists of merely a mesh 51 and a film 52 deposited thereupon. It thus represents an extreme case, as it contains one layer (the mesh 51) with very great porosity, while the other layer (the film 52) has an insignificantly small porosity.

Figure 6:
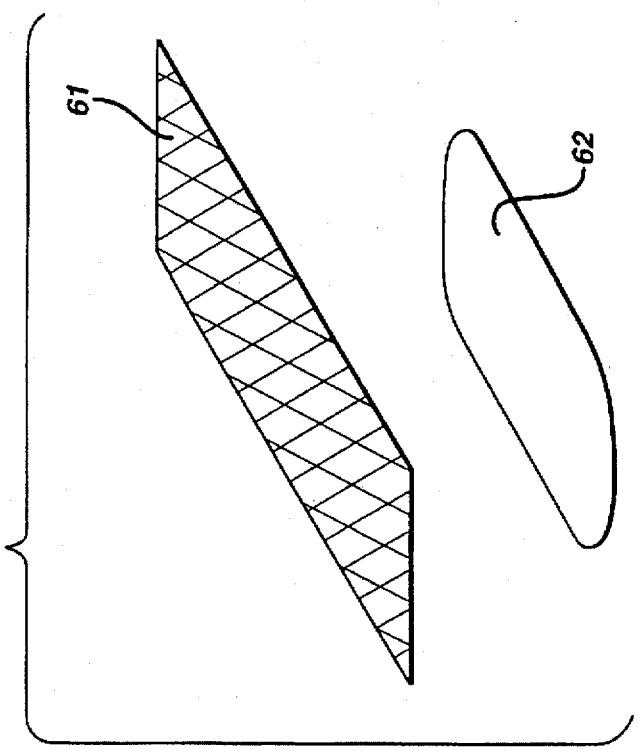

In FIG. 6, the version from FIG. 5 is somewhat modified. The film 62 now covers only a part of the mesh 61.

Figure 7:
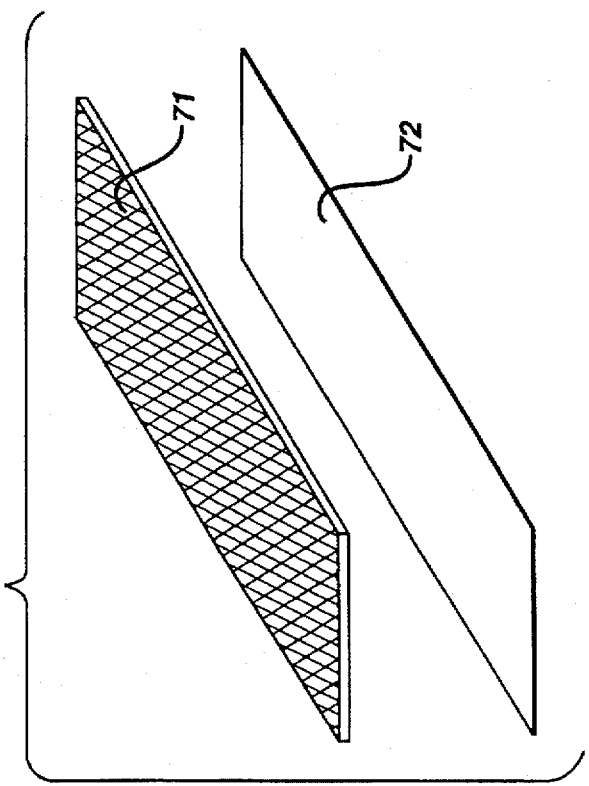

The version shown in FIG. 7 does not contain a stabilizing mesh. The implant consists of merely a fleece 71 with a porosity of 1000 l/m² s and a film 72. Such a version is suitable for example as a resorbable implant for the bone area close to the teeth during the treatment of parodontosis. If the implant is placed so that the film 72 lies on the gums side, this effectively prevents the rapidly-growing gum from penetrating the bone area. The bone substance thus has enough time to grow into the fleece 71. In this way, a sound bone area again builds up.

Figure 8:
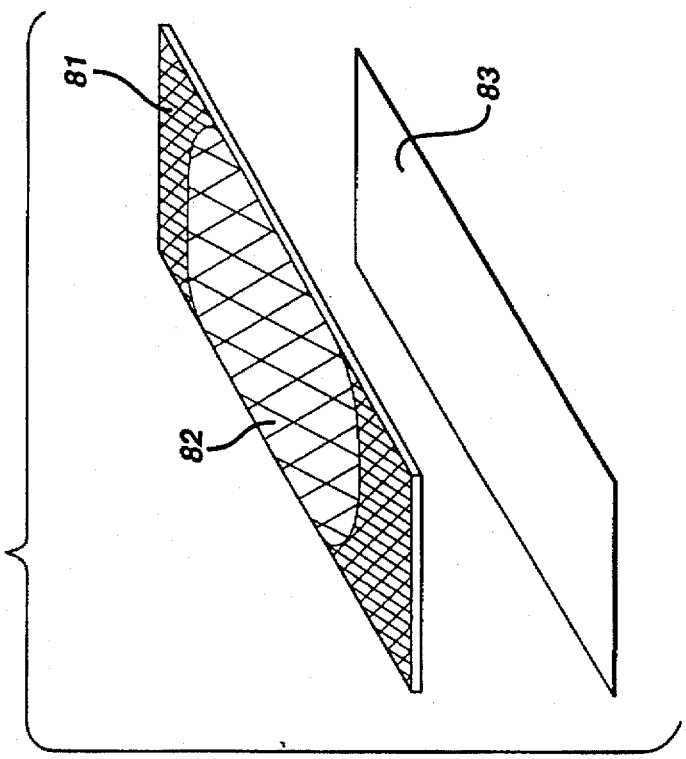

The version represented in FIG. 8 is similar to that in FIG. 7. Here, a fleece layer comprises two zones, namely a zone 81 consisting of a fleece with a porosity of 1000 l/m² s and a zone 82 consisting of a fleece with a porosity of 500 l/m² s. One side of the fleece layer is covered by a film 83.

Figure 9:
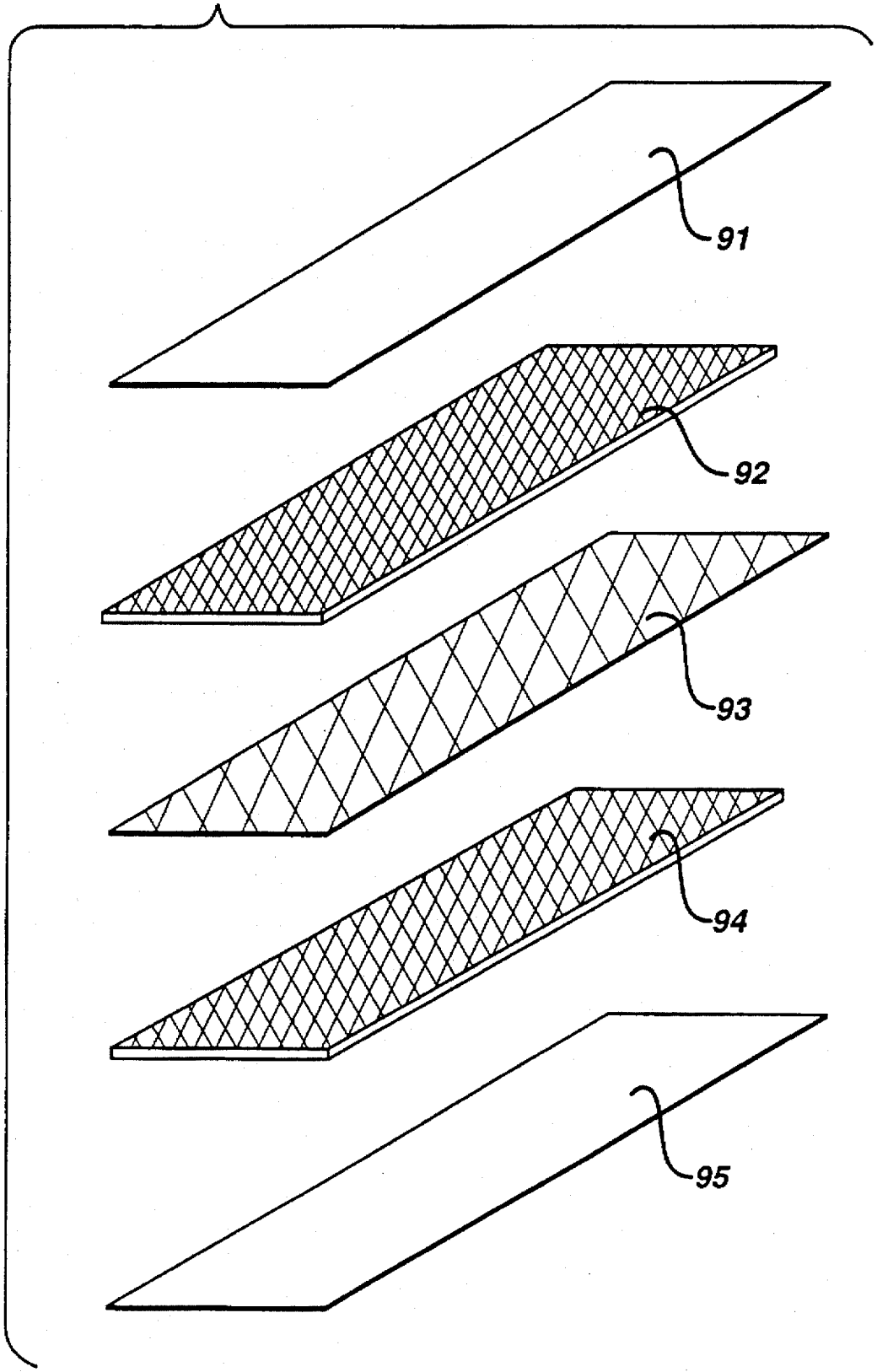

FIG. 9 shows a version which again contains a mesh 93 provided as a middle layer. On one side of the mesh 93 is a fleece 92 with a porosity of 100 l/m² s, which is covered by a film 91. Deposited on the other side of mesh 93 is a fleece 94 with a porosity of 500 l/m² s, which is provided with a final film 95.

FIG. 10 shows a complex structure of a multi-layered implant according to the invention. A mesh 104 serves as support. On the upper side of the mesh 104 is a fleece layer with an outer zone 102, consisting of a fleece with the porosity 200 l/m² s, and an inner zone 103, whose fleece has a porosity of 100 l/m² s. Part of the inner zone 103 is covered by a film 101. Deposited on the underside of the mesh 104 is a fleece layer with the zones 105 (porosity 250 l/m² s) and 106 (porosity 150 l/m² s). Part of the zone 106 is covered by a film 107.

For the sake of clarity, the multi-layered implants shown in the Figures have a rectangular basic shape and constant thickness of the fleece layers. However, for a given use, the basic make-up of the implant, the material and the porosity of the individual layers, as well as the thickness of the layers and the overall shape of the implant are matched to the conditions.

To combine the individual layers of the multi-layered implant according to the invention with one another, materials with different melting points can for example be used for adjoining layers; if, during manufacture, the implant is heated to a temperature which is higher than the melting point of the material with the lower melting point, but below the melting point of the material with the higher melting point, one of the layers melts and combines with the adjoining layer. For implants made from resorbable material, preferably from Polydioxanone and Polyglactin, the principle is described in DE 38 30 005 C1.

It is also possible to place a film made from the material with the lower melting point between two layers having different melting points and then carry out heating so that the film melts and becomes porous and the two layers are bonded to each other. In this way, for example, a mesh made from a non-resorbable material and a porous fleece layer made from a resorbable material with a lower melting point can be connected to each other.

We claim:

1. A surgical implant, consisting of:

a woven mesh having a top side and a bottom side; and a porous fleece layer mounted to the top side of the mesh wherein said fleece has a porosity in the range of about 100 to about 1,000 liters/(m²s) gas low measured at an inlet pressure of 200 PA, a test surface of 50 cm² and a test thickness of 1 mm, wherein the woven mesh and porous fleece layer are made of a resorbable polymer selected from the group consisting of Polyglactin 910, Polydioxanone, Poliglecaprone 25 and combinations thereof.

2. The implant of claim 1, wherein the fleece layer has a first zone having a porosity of 1000 l/m²s and a second adjacent peripheral zone having a porosity of 200 l/m²s.

* * * * *